US 6,731,379 B2

(12) United States Patent
Caputo et al.

(10) Patent No.: US 6,731,379 B2
(45) Date of Patent: May 4, 2004

(54) METHOD AND DEVICE FOR DETERMINING THE CONCENTRATION OF HEPARIN IN A SAMPLE OF FLUID

(75) Inventors: Giuseppe Caputo, Turin (IT); Raffaele Castelli, Mirandola (IT); Elena Comoglio, Turin (IT); Leopoldo Della Ciana, Ivrea (IT); Arnaldo Giannetti, Crescentino (IT)

(73) Assignee: Dideco S.p.A., Mirandola (IT)

( * ) Notice: Subject to any disclaimer, the term of this patent is extended or adjusted under 35 U.S.C. 154(b) by 15 days.

(21) Appl. No.: 10/634,169

(22) Filed: Aug. 5, 2003

(65) Prior Publication Data

US 2004/0027557 A1 Feb. 12, 2004

Related U.S. Application Data

(63) Continuation of application No. 09/686,219, filed on Oct. 11, 2000, now Pat. No. 6,630,989.

(30) Foreign Application Priority Data

Oct. 12, 1999 (IT) .......................................... TO99A0882

(51) Int. Cl.[7] ............................................... G01N 33/49
(52) U.S. Cl. ......................... 356/39; 356/409; 600/322
(58) Field of Search ............................. 356/39–41, 409, 356/407, 414; 600/322

(56) References Cited

U.S. PATENT DOCUMENTS

| | | | |
|---|---|---|---|
| 4,003,892 A | 1/1977 | Lohr et al. | |
| 4,448,188 A | 5/1984 | Loeb | 600/108 |
| 4,619,639 A | 10/1986 | Nosé et al. | 604/8 |
| 4,911,549 A | 3/1990 | Karkar | |
| 5,830,134 A | 11/1998 | Caputo et al. | |

OTHER PUBLICATIONS

Lewis, Richard J., Sr., ed., *Hawley's Condensed Chemical Dictionary, Thirteenth Edition*, John Wiley & Sons, Inc., New York, 1997, p. 687.

Tas, "Polyacrylamide Films as a Tool for Investigating Qualitative and Quantitative Aspects of the Staining of Glycosaminoglycans with Basic Dyes," *Histochemical Journal*, 9:267–276 (1977).

Templeton, "General Occurrence of Isosbestic Points in the Metachromatic Dye Complexes of Sulfated Glycosaminoglycans," *International Journal of Biological Macromolecules*, 10:131–136 (1988).

*Primary Examiner*—Richard A. Rosenberger
*Assistant Examiner*—Vincent P. Barth
(74) *Attorney, Agent, or Firm*—Popovich, Wiles & O'Connell, P.A.

(57) ABSTRACT

A device for determining the concentration of heparin in a fluid sample comprising: a container for holding the fluid sample; a container for holding the dye solution; a mixer for mixing the fluid sample and the dye solution; an illumination source for illuminating a mixture comprising the fluid sample and the dye solution with electromagnetic radiation having a substantially continuous range of wavelengths in the visible range; a detector for detecting the absorption spectrum of the mixture within the substantially continuous range of wavelengths; a recorder for recording the absorption spectrum of the mixture within the substantially continuous range of wavelengths; and a calculator for calculating a spectral parameter.

6 Claims, 8 Drawing Sheets

Thionine

Azure C

Azure A

Azure B

Methylene blue

Toluidine blue

Purified Azure A

METHOD AND DEVICE FOR DETERMINING THE CONCENTRATION OF HEPARIN IN A SAMPLE OF FLUID

This application is a continuation of U.S. application Ser. No. 09/686,219, filed Oct. 11, 2000, now U.S. Pat. No. 6,630,989, the contents of which are hereby incorporated herein by reference.

FIELD OF THE INVENTION

The present invention relates to a method of determining the concentration of heparin in fluid samples, and to a device for performing the method.

BACKGROUND OF THE INVENTION

Heparin is a heteropolysaccharide of the acid mucopolysaccharide type which has anticoagulant activity resulting from its ability to catalyze the reaction between antithrombin III and thrombin. On the basis of this activity, heparin is widely used as an anticoagulant in cardiovascular surgery, for example, during operations with extracorporeal circulation, and in other diagnostic and therapeutic applications.

When beparin is used as an anticoagulant, it may be very useful to have available a method which permits rapid, reproducible and accurate measurement of the concentration of heparin present in the sample of interest, and a device for performing this measurement. In order to perform this measurement, it is known to use dyes of the cationic thiazines series. As a result of the reaction of these dyes with heparin, it is possible to observe a change in the absorption (or transmission) spectrum of the dye, that is, a reduction in the absorption due to the free dye in solution and the appearance of an absorption band of the heparin-dye complex formed. The absorption spectrum of cationic thiazines in dilute aqueous solution is in fact characterized by a main absorption band due to the contribution of the monomer and the dimer of the dye in solution. When heparin is added to this dilute solution, a second band (called the $\mu$ band) which corresponds to the heparin-dye complex formed appears in the absorption spectrum of the solution. The addition of heparin to the dye solution not only causes the appearance of the $\mu$ band, but also causes a reduction in the absorption of the main band. The reduction in the absorption of the free dye in solution and the increase in the absorption of the dye-heparin complex constitute the two components of a phenomenon known by the term "metachromasia", the magnitudes of which, in suitable reaction conditions, can be correlated with the concentration of heparin present in the sample.

On the basis of this principle, assays have been developed for measuring the concentration of heparin in samples of interest. U.S. Pat. No. 4,911,549 (Karkar) describes a method of determining the heparin concentration in blood plasma by metachromatic reaction with the dye Azure A which belongs to the cationic thiazines series. This assay is based on the measurement of two distinct transmittance signals for two distinct wavelengths, one of which is substantially insensitive to the heparin dilution.

SUMMARY OF THE INVENTION

It has surprisingly been found that the measurement of the entire absorption spectrum of the dye in a metachromatic heparin assay, rather than measurement of distinct absorption signals with predetermined separate wavelengths, achieves results which are more accurate and reproducible and, above all, are independent of the reaction medium. In the case of assays performed on samples of biological fluids such as blood plasma containing proteins and other chemical species which could potentially interfere with accurate measurement of the absorption at these predetermined wavelengths, this latter characteristic is of substantial importance because it makes possible a device which can perform the assay automatically and which does not require repeated calibrations.

Accordingly, the invention provides a method for determining the concentration of heparin in a fluid sample comprising: (a) providing a fluid sample containing heparin; (b) adding to the fluid sample a solution of a dye to form a mixture of sample and dye, wherein the dye interacts with the heparin in the sample so that the absorption spectrum of the mixture of sample and dye in the visible range varies as a result of the interaction in a manner quantitatively dependent on the heparin concentration; (c) determining the absorption spectrum in the visible range of the mixture of sample and dye; and (d) calculating a spectral parameter representative of both the reduction in the absorption of the free dye in solution and the increase in the absorption of the dye-heparin complex, the value of the spectral parameter being indicative of the concentration of heparin present in the fluid sample, in order to determine the concentration of heparin present in the fluid sample. The relationship between the value of the spectral parameter and the concentration of the heparin present in the fluid sample has been previously determined by determining the absorption spectra, in the visible range, of a composition comprising the fluid and the dye, in the absence of heparin and in the presence of a plurality of concentrations of heparin, and calculating the relationship between the value of the spectral parameter and the concentration of heparin. A device for performing this method is also provided.

Additional features and advantages of the invention are set forth in the description which follows and in part will be apparent from the description. The objectives and other advantages of the invention will be realized and attained by the method of determining the concentration of heparin in a fluid sample and the device for performing this method as particularly pointed out in the written description and claims.

It is to be understood that both the foregoing general description and the following detailed description are exemplary and explanatory and are intended to provide further explanation of the invention as claimed.

DETAILED DESCRIPTION OF THE INVENTION

Figure 1:
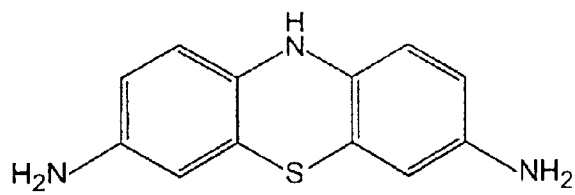
FIG. 1 shows the structures of thionine, Azure A, Azure B, Azure C, methylene blue, and toluidine blue, which are dyes that can be used in the invention.
Figure 1:
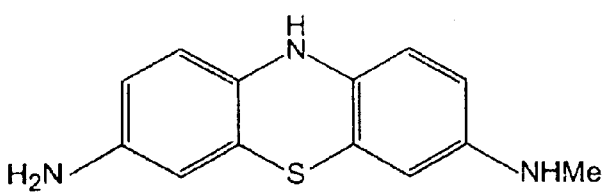
Figure 1:
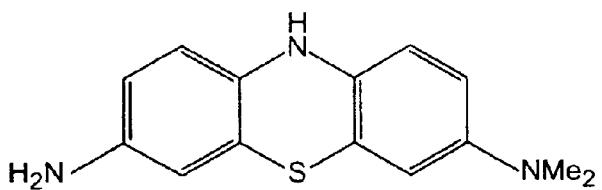
Figure 1:
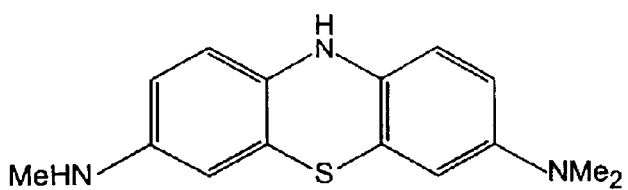
Figure 1:
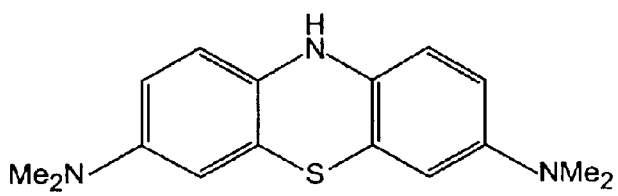
Figure 1:
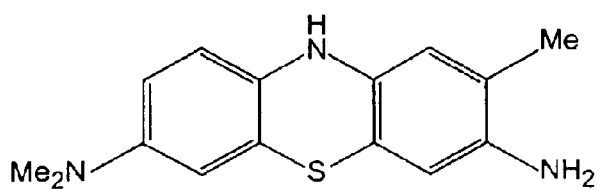

The invention provides a method for determining the concentration of heparin in a fluid sample comprising: (a) providing a fluid sample containing heparin; (b) adding to the fluid sample a solution of a dye to form a mixture of sample and dye, wherein the dye interacts with the heparin in the sample so that the absorption spectrum of the mixture of sample and dye in the visible range varies as a result of the interaction in a manner quantitatively dependent on the heparin concentration; (c) determining the absorption spectrum in the visible range of the mixture of sample and dye; and (d) calculating a spectral parameter representative of both the reduction in the absorption of the free dye in solution and the increase in the absorption of the dye-heparin complex, the value of the spectral parameter being indicative of the concentration of heparin present in the fluid sample, in order to determine the concentration of heparin present in the fluid sample. The relationship between the value of the spectral parameter and the concentration of the heparin present in the fluid sample has been previously determined by determining the absorption spectra, in the visible range, of a composition comprising the fluid and the dye, in the absence of heparin and in the presence of a plurality of concentrations of heparin, and calculating the relationship between the value of the spectral parameter and the concentration of heparin. In a preferred embodiment, the fluid sample is serum or blood plasma.

In one embodiment of the invention, the spectral parameter is the area under the absorption spectrum in the visible range of the mixture of sample and dye. In another embodiment of the invention, the spectral parameter is the difference in the area under the absorption spectrum in the visible range of the mixture of sample and dye and the area under the absorption spectrum in the visible range of a second fluid sample to which no heparin has been added. In a preferred embodiment, the second fluid sample to which no heparin has been added is a sample from a patient before heparin has been administered to the patient and the fluid sample is a sample from the patient after heparin has been administered to the patient. In still another embodiment of the invention, the spectral parameter is a portion of the area under the absorption spectrum in the visible range such that the variation of the portion of the area is indicative of the concentration of heparin present in the fluid sample.

In another embodiment of the invention, the spectral parameter is the RD parameter, defined by the formula:

$$RD = A_{\lambda 1}/A_{\lambda 2}$$

in which $A_{\lambda 1}$ and $A_{\lambda 2}$ are the absorbance values measured at two different wavelengths $\lambda 1$ and $\lambda 2$, respectively, and in which $\lambda 1$ is selected such that the value of $A_{\lambda 1}$ decreases proportionally with the heparin concentration, and $\lambda 2$ is selected such that the value of $A_{\lambda 2}$ increases proportionally with the heparin concentration.

Because the method of the present invention utilizes both of the components of the metachromasia phenomenon, it achieves a high degree of sensitivity and a low detection limit of the assay. The metachromatic assay of the present invention provides for the use of a source which can emit electromagnetic radiation having a substantially continuous spectrum of wavelengths in the visible range. It is thus possible both to obtain the entire absorption spectrum of the sample of interest (that is, the absorption values throughout the spectrum of wavelengths of the radiation emitted by the source used) and subsequently to select the wavelengths which are particularly significant in the specific assay conditions. Clearly, the selection of specific wavelengths from the entire absorption spectrum is not equivalent to the use of predetermined specific wavelengths.

According to one embodiment of the present invention, the variation of the spectral parameter brought about as a result of the interaction between heparin and dye is the variation of the area under the absorption spectrum in the visible range of a composition comprising the fluid and the dye in the presence and in the absence of heparin. This variation is indicative of the concentration of heparin present in the fluid sample. In the method according to the invention, the heparin concentration is preferably expressed in IU/ml.

The term "area" is intended to define either the area under each absorption spectrum in the entire visible range, or a portion of this area selected in a manner such that it is representative of both components of the metachromasia phenomenon and its variation is thus indicative of the concentration of heparin present in the fluid sample.

Equivalent performance of the test according to the invention can be achieved by measuring the variation in the presence and in the absence of heparin of another spectral parameter which is also indicative of the concentration of heparin present in the fluid sample, that is, the variation of the RD parameter, defined as:

$$RD = A_{\lambda 1}/A_{\lambda 2}$$

in which $A_{\lambda 1}$ and $A_{\lambda 2}$ are the absorption values measured at wavelengths $\lambda 1$ and $\lambda 2$, respectively and in which $\lambda 1$ is selected such that the value of $A_{\lambda 1}$ decreases proportionally with the heparin concentration whereas $\lambda 2$ is selected such that the value of $A_{\lambda 2}$ increases proportionally with the heparin concentration. In other words, within the absorption spectrum in the visible range of the composition comprising the fluid and the dye, two wavelengths ($\lambda 1$ and $\lambda 2$) are selected such that each is representative of one of the two components of the metachromasia phenomenon defined above.

The values of $\lambda 1$ and $\lambda 2$ selected from the absorption spectrum are such as to be optimal in relation to the dye used and to the specific assay conditions. Preferred values of $\lambda 1$ and $\lambda 2$ fall, for example, within the ranges of 560 to 610 nm and 480 to 530 nm, respectively; within these wavelength ranges, for example, 590 nm and 510 nm, respectively, are more preferred.

A method as described above in which transmittance measurements are performed also falls within the scope of the present invention since transmittance (T) is linked to absorbance (A) by the following equation:

$$A = \log_{10}(1/T).$$

The dye solution can comprise a non-ionic surfactant. The concentration of the dye present in the solution is preferably within the range of $1 \times 10^{-3}$ to $1 \times 10^{-6}$ moles/liter, more preferably about $5 \times 10^{-5}$ moles/liter. The ionic strength of the dye solution is preferably less than 0.1. Moreover, the dye solution is preferably added to the fluid sample in a proportion of from 5:1 to 100:1 by volume, according to the dye used and the dynamic range required. More preferably, the proportion is 10:1.

The dye used in the metachromatic assay of the invention is preferably a cationic thiazine selected from thionine, Azure A, Azure B, Azure C, methylene blue, toluidine blue and mixtures thereof, preferably of known composition. The structures of these molecules are shown in FIG. 1.

The use of Azure A is more preferred, even more preferably with a degree of purity of from 90 to 100%, and still more preferably with a degree of purity of 95 to 99%. In embodiments of the invention, the concentration of Azure A in the dye solution is within the range of from $1\times10^{-3}$ to $1\times10^{-6}$ moles/liter, more preferably about $5\times10^{-5}$ moles/liter. In other embodiments of the invention, the dye is Azure A and $\lambda 1$ is selected within the range of from 560 to 610 nm and $\lambda 2$ is selected within the range of from 480 to 530 nm, more preferably, $\lambda 1$ is 590 nm and $\lambda 2$ is 510 nm.

As reported in U.S. Pat. No. 4,003,892 (Löhr et al.), commercial cationic thiazines of the methylene blue homologous series are in fact actually compositions comprising at least two members of the group consisting of thionine, Azure A, Azure B, Azure C and methylene blue in variable proportions. Each of these dyes is in fact produced by oxidative demethylation starting with methylene blue (the molecule of the series with the highest degree of N-methylation) which produces a complex mixture comprising the molecule desired and other thiazines of the same series in variable proportions.

These dyes of the methylene blue homologous series have been purified by chromatography in silica-gel columns with the use of a mixture of water, acetic acid and formic acid as an eluent, as described in the patent mentioned above and in greater detail in Example 1.

Each of the five fractions thus obtained (each of which represents a single cationic thiazine) was further subjected to reverse phase HPLC chromatography with the use of a decreasing polarity gradient in order to evaluate its degree of purity. In the case of Azure A, a degree of purity greater than 90% was assessed. In the method according to the invention, the use of Azure A with a degree of purity of from 95 to 99% is therefore even more preferred.

Figure 2A:
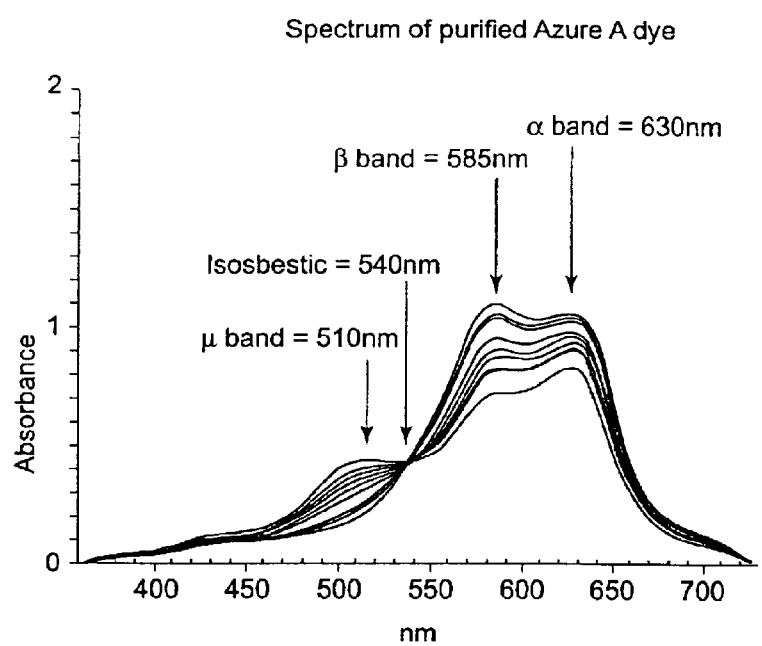
FIG. 2a shows the spectra obtained from a solution comprising purified Azure A and various concentrations of heparin within a range of 0 to 10 IU/ml.

If the spectrum of the purified Azure A dye is analyzed, the appearance of a new absorption band with a maximum at about 590 nm is observed. This band, known as the β band, is due to the absorption solely of the dimer of the dye in solution. Moreover, in the purified Azure A spectrum, the maximum absorption band at 630 nm (the α band) which is already visible in the spectrum of the non-purified dye, in which it was indicated as the main band, is considerably narrower. In the spectrum of the purified dye, the contributions of the dimer (β band) and of the monomer (α band) of the dye can thus be clearly distinguished. If the spectra of the purified Azure A dye in the presence of heparin are analyzed, it becomes clear that the region corresponding to the β band is also involved in the metachromasia phenomenon, since the absorbance within this region varies in a manner quantitatively dependent on the concentration of heparin present in the fluid sample. FIG. 2a shows the spectra obtained from a solution comprising purified Azure A and various concentrations of heparin within a range of 0 to 10 IU/ml.

Figure 2B:
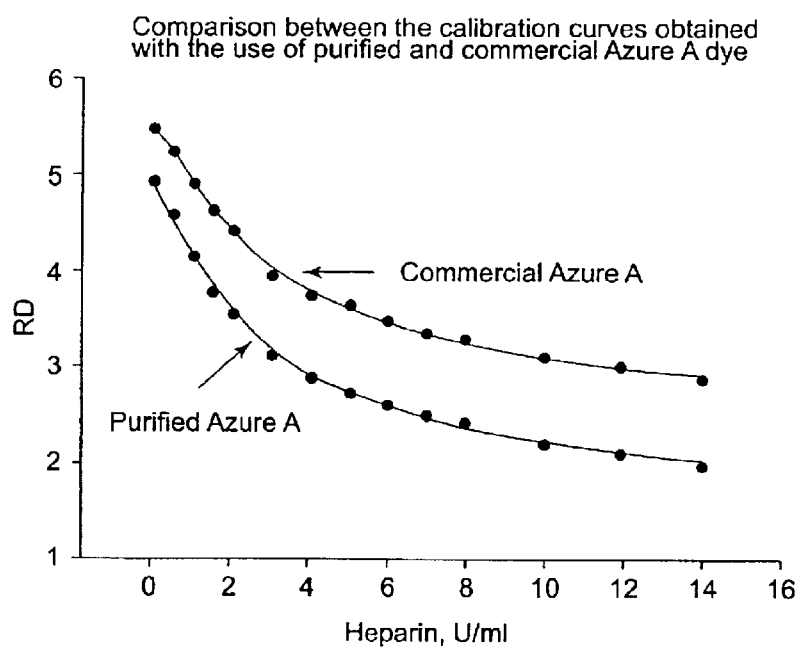
FIG. 2b shows a comparison between the calibration curves obtained with the use of the method based on the calculation of the RD parameter and with the use of purified and non-purified Azure A.

The use of the Azure A dye purified as described above and in greater detail in Example 1 below increases the sensitivity of the assay. FIG. 2b is a comparison between the calibration curves obtained with the use of the method based on the calculation of the RD parameter and with the use of purified and non-purified Azure A. The steeper slope of the curve obtained with the use of purified Azure A illustrates the increase in sensitivity obtained for given assay conditions.

The invention provides a device for determining the concentration of heparin in a fluid sample, comprising:

a container for holding the fluid sample;

a container for holding the dye solution;

a mixer for mixing the fluid sample and the dye solution;

an illumination source for illuminating a mixture comprising the fluid sample and the dye solution with electromagnetic radiation having a substantially continuous range of wavelengths in the visible range;

a detector for detecting the absorption spectrum of the mixture within the substantially continuous range of wavelengths;

a recorder for recording the absorption spectrum of the mixture within the substantially continuous range of wavelengths; and a calculator for calculating a spectral parameter;

wherein the value of the spectral parameter is indicative of the concentration of heparin present in the fluid sample, and the spectral parameter is representative of both the reduction in the absorption of the free dye in solution and the increase in the absorption of the dye-heparin complex in a method in which the dye solution is added to the fluid sample to form a mixture of sample and dye, and the dye interacts with the heparin in the sample so that the absorption spectrum of the mixture of sample and dye in the visible range varies as a result of the interaction in a manner quantitatively dependent on the heparin concentration.

In an embodiment of the invention, the illumination source for illuminating the composition comprises at least one light-emitting diode having substantially continuous multiple wavelengths in the visible range. In another embodiment, the illumination source further comprises at least one diode emitting light in the red region (for example, between 620 and 750 nm).

In an embodiment of the invention, the container for holding the fluid sample comprises a hollow fiber filter with a porosity to separate the corpuscular portion of blood from the plasma. In another embodiment, the device further comprises a holder for holding a detergent solution and a holder for holding a waste solution. The device can further comprise a computer.

The following examples are provided by way of illustration but are not intended to limit the scope of the present invention in any way.

Example 1

Purification of Azure A dye

The purification of the components of the methylene blue homologous series was performed with the use of the method described by Löhr et al, in U.S. Pat. No. 4,003,892, modified so as to improve it, particularly in terms of yield and recovery of the eluent.

2.5 g of commercial Azure A (Aldrich) dissolved in 75 ml of eluent (10% acetic acid and 5% formic acid in aqueous solution) was supplied to a Merck 60 240–400 mesh silica-gel column. The dimensions of the column were 50 mm diameter and 1000 mm height. The flow was 6 ml/min.

In these conditions, six fractions, each corresponding to a dye in the methylene blue homologous series were separated:

| Fraction 1 | Bernthsen violet | A = 580 nm |
| Fraction 2 | Thionine | A = 600 nm |
| Fraction 3 | Azure C | A = 613 nm |
| Fraction 4 | Azure A | A = 630 nm |
| Fraction 5 | Azure B | A = 650 nm |
| Fraction 6 | Methylene blue | A = 670 nm |

Fraction 4 (Azure A) was diverted and adsorbed in a Supelco XAD 2 column with a flow of 1 ml/min. The dimensions of the column were 40 mm diameter and 350 mm height. During this adsorption stage in particular it is preferable to avoid light as much as possible; this was achieved by covering the apparatus and particularly the columns with aluminium foil.

After the Azure A had been fully adsorbed, the column was washed with 1 litre of a 5% NaCl solution so as to exchange the organic anions with Cl⁻. The column was then washed with distilled water until a negative chlorides reaction (reaction with $AgNO_3$) was obtained. This washing was performed with a counterflow to prevent loss of dye. After the washing, the Azure A dye was eluted with pure methanol. The methanolic solution of Azure A was evaporated to approximately 10 ml, filtered and added dropwise to an excess of ether (about 500 ml) from which the solid Azure A precipitated. The yield of the method was about 50% by weight.

The silica-gel column can be regenerated by washing with distilled water, a 3% solution of potassium permanganate in water, followed by a 3% sodium dithionite, sulphite or metabisulphite solution, distilled water again and, finally, re-equilibration with the 10% acetic acid/5% formic acid solution.

It is also possible to regenerate 70–80% of the eluent by passing the fractions containing the dyes, except for the Azure A dye, through a column of activated carbon (30–250 mm) which captures the dyes, leaving the eluent clean.

Example 2

Metachromatic Assay for Heparin with the Use of Purified Azure A Dye, Areas Method 1 ml of a $5\times10^{-5}$ moles/liter solution, in deionized water water also including 1% v/v of a non-ionic surfactant (Pluronic F68, a polyoxyalkylene made by BASF Aktiengesellschaft, Ludwigshaven, . Germany), of Azure A (Aldrich) purified in accordance with Example 1 was added to a 100 μl sample of horse serum (Sigma) containing an unknown concentration of added sodium heparin (Liquemin, Roche) expressed in IU/ml.

The composition thus produced was mixed for a few seconds and transferred to an optical cuvette for the detection of the absorption spectrum. For this purpose, a Perkins Elmer spectrophotometer model Lambda 2 with a tungsten lamp was used. The spectrophotometer was connected to a personal computer for acquiring and processing the data. The area under the absorption spectrum of the sample between 400 nm and 800 nm was calculated by integration.

The same method was repeated with a composition comprising 100 μl of the same serum without added heparin, and 1 ml of a dye solution as defined above.

Figure 3A:
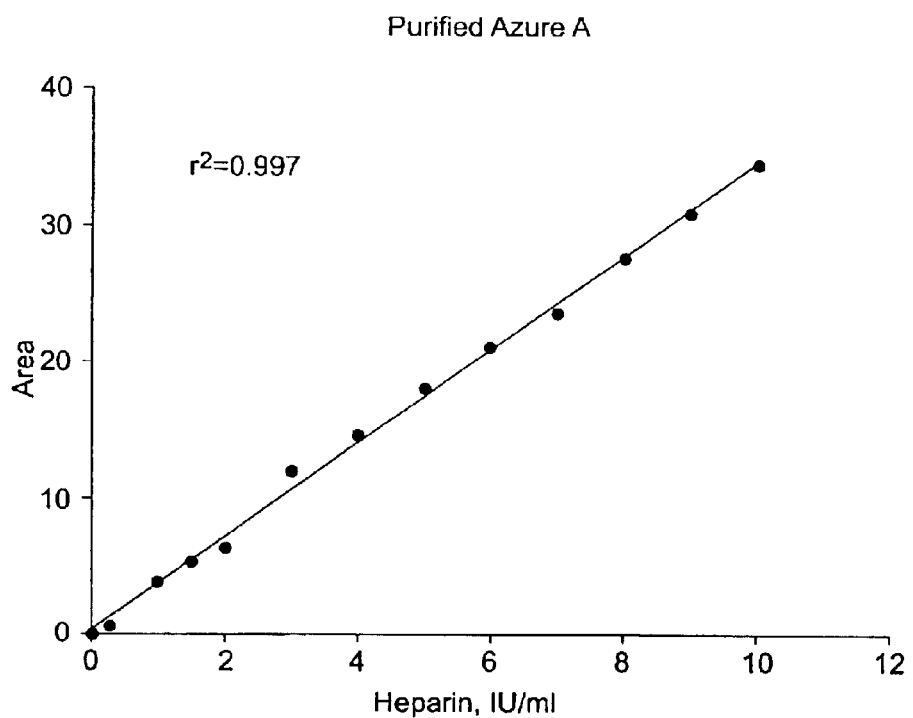
FIG. 3a shows the calibration curve obtained in Example 2.
Figure 3B:
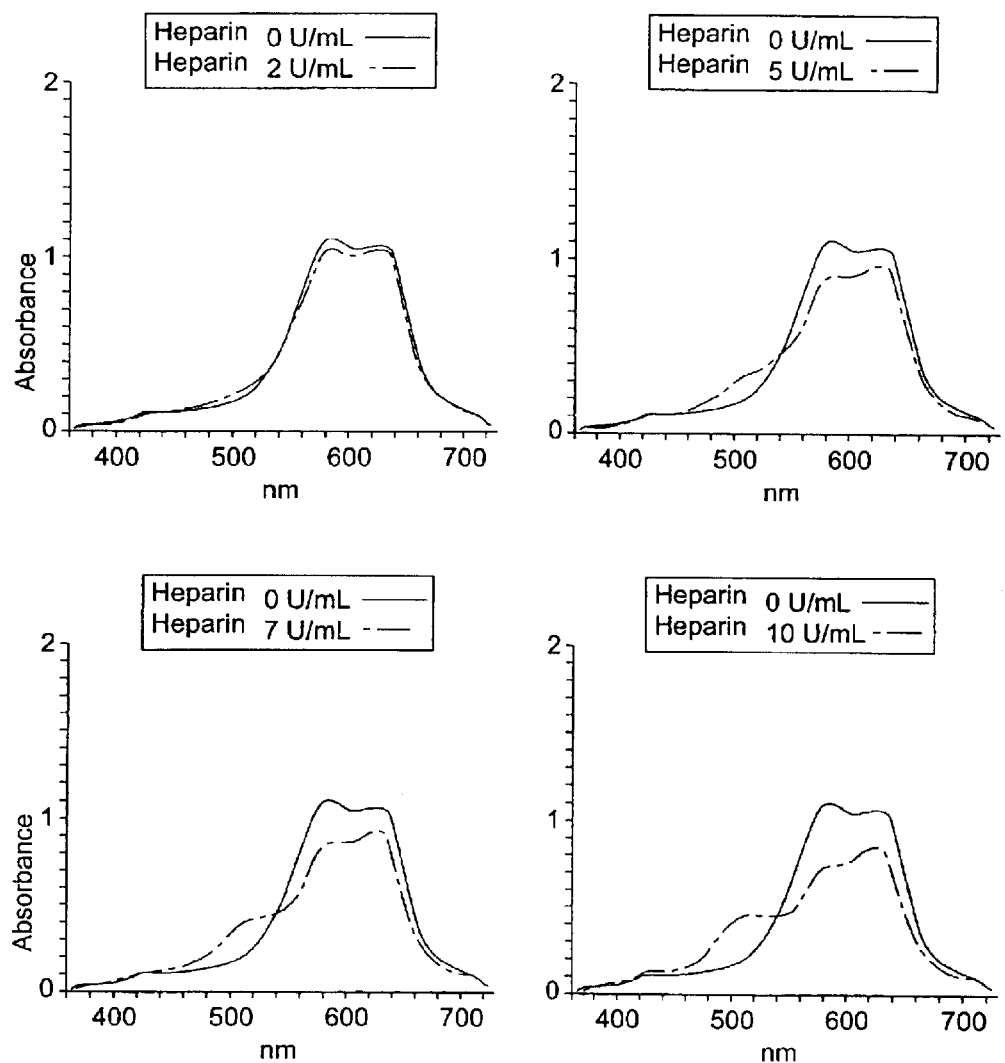
FIG. 3b shows the change in area under the absorption spectrum of an Azure A solution in the absence of heparin and in the presence of heparin at concentrations of 2, 5, 7 and 10 IU/ml, respectively.

The change in the area under the two absorption spectra obtained was calculated and this numeric value was used to calculate the concentration of heparin present in the serum sample with the use of a calibration curve constructed beforehand using serum samples containing different known heparin concentrations. FIG. 3a shows the calibration curve obtained. FIG. 3b comprises four graphs showing the change in the area under the absorption spectrum of an Azure A solution in the absence of heparin and in the presence of heparin at concentrations of 2, 5, 7 and 10 IU/ml, respectively.

The detection limit of the assay, defined as the concentration of analyte which produces a signal of an intensity equal to $2.58\sigma_0$ (in which $\sigma_0$ is the standard deviation of the signal obtained in the absence of heparin) was 0.1 IU/ml. Within the heparin concentration range of from 0 IU/ml to 10 IU/ml, a sensitivity of the assay of 3.44 (units of area)×(IU/ml)$^{-1}$ was calculated.

Example 3

Metachromatic Assay for Heparin with the Use of Purified Azure A Dye, Method Based on Calculation of the RD Parameter Azure A dye purified as described in Example 1 was used to determine the concentration of heparin in a fluid sample (serum) with the use of the method based on the calculation of the RD parameter as defined above. Values of λ1 and λ2 which had been found to be optimal for the specific assay conditions, that is 590 nm and 510 nm, respectively, were used. The value of RD was thus calculated by the formula:

$$RD = A_{590\,nm}/A_{510\,nm}$$

Figure 4:
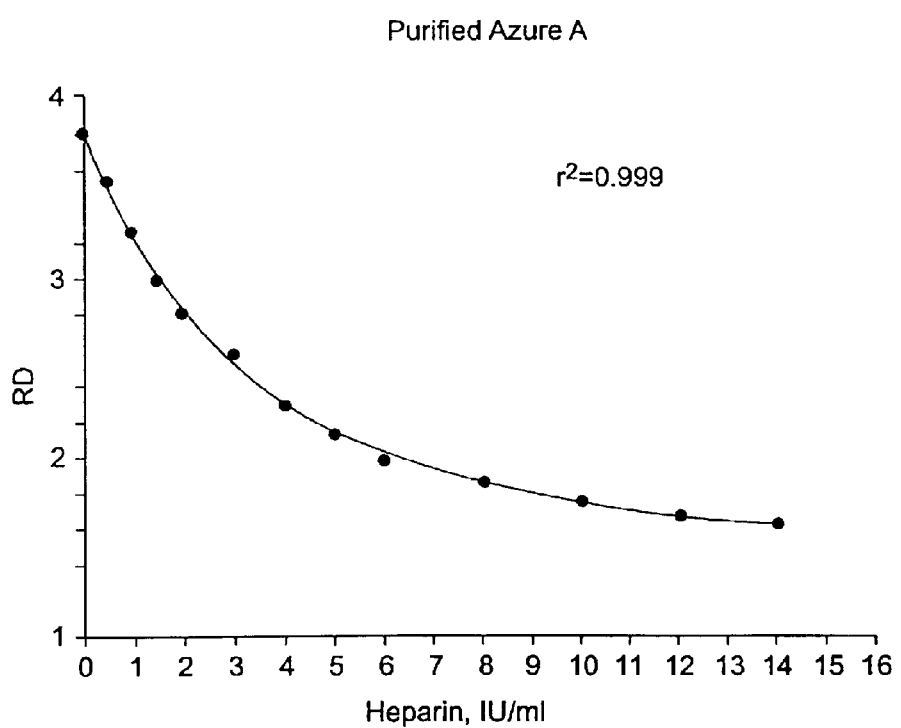
FIG. 4 shows the calibration curve obtained in Example 3.

Both of the values of $A_{590\,nm}$ and $A_{510\,nm}$ were also corrected for the absorbance value at the base line of the spectrum ($A_{800\,nm}$). FIG. 4 shows the calibration curve obtained. The detection limit of the assay was 0.1 IU/ml. The sensitivity of the assay, calculated within the range of heparin concentration of from 0 IU/ml to 3 IU/ml, was 2.54 (Units of RD)×(IU/ml)$^{-1}$.

Example 4

Metachromatic Assay for Heparin with the Use of Toluidine Blue, Areas Method

Figure 5:
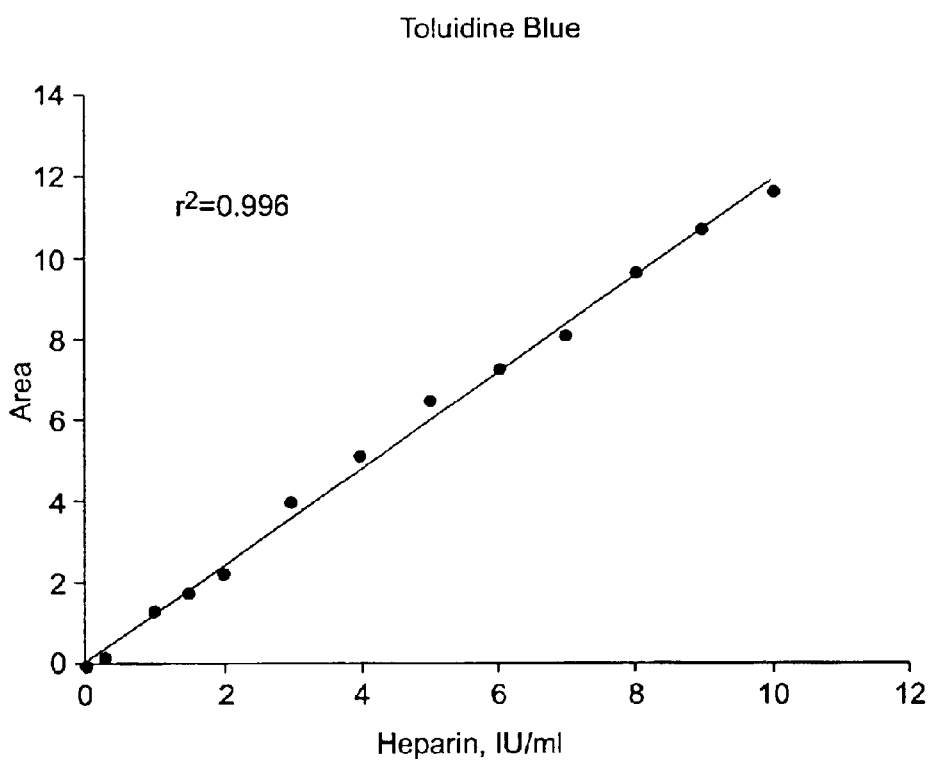
FIG. 5 shows the calibration curve obtained in Example 4.

The metachromatic assay according to the, method described in Example 2 was performed with the use of the commercial dye toluidine blue (Aldrich). The assay conditions were those described in Example 2 above, except that the determination was performed on a sample of bovine plasma. FIG. 5 shows the calibration curve obtained. The sensitivity of the metachromatic assay according to this embodiment within the range of heparin concentrations of from 0 IU/ml to 10 IU/ml was 1.19 (Units of area)×(IU/ml)$^{-1}$.

Example 5

Integrated System

Figure 6:
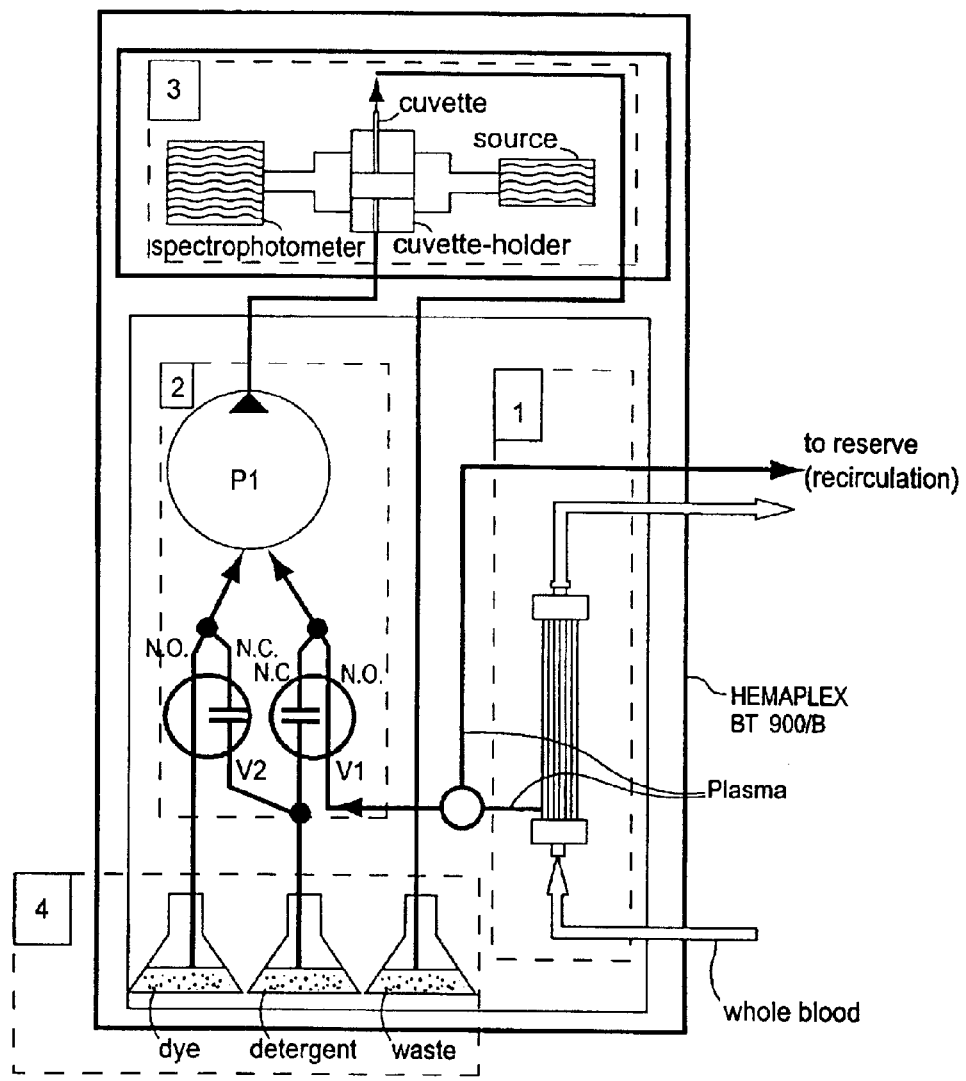
FIG. 6 shows a schematic of an integrated system, a device of the invention.

FIG. 6 shows an embodiment of a device according to the invention. This device, known as an "integrated system" is particularly suitable for performing the metachromatic assay for heparin according to the invention on a sample of blood plasma from a patient undergoing a surgical operation with extracorporeal circulation. The device is constituted by four separate sections:

(1) Blood treatment section: constituted by a filter, for example, a filter of hollow polypropylene fibres with a pore diameter of 0.55 μm and an effective filtration area of 0.1 m² (Hemaplex X® BT 900, Dideco), connected in parallel with a circuit for extracorporeal circulation. This filter separates the corpuscular portion of the blood from the plasma without interfering with the heparin concentration present in the plasma.

(2) Metering section: constituted by a peristaltic pump (P1) with two channels and two pinch valves (V1 and V2). The tubes used were of Tygon® with the following cross-sections: ID 3/32", OD 5/32", WALL 1/32" for the dye, and ID 1/32", OD 3/32", WALL 1/32" for the plasma. This section has the function of metering both the plasma coming from the filter and the dye solution in order to produce a composition comprising plasma and dye, and also of admitting a detergent solution into the device to clean the device when necessary.

(3) Measurement section: constituted by a cuvette-holder, a cuvette, a source of electromagnetic radiation in the visible range, and an optical-fibre spectrophotometer. The holder is constructed for housing the cuvette, engaging the source of electromagnetic radiation and of the optical fibre spectrophotometer, and collimating the beam of electromagnetic radiation in the cuvette.

(4) Liquids section: constituted by a container for the dye solution, a container for the detergent solution and a container for collecting the waste solutions.

The metering section of the device is controlled electronically, preferably by two electronic cards. The device is also connected to a personal computer for the control of the metering section and the acquisition and processing of the data coming from the spectrophotometer.

The above description and accompanying drawings are provided for the purpose of describing embodiments of the invention and are not intended to limit the scope of the invention in any way. It will be apparent to those skilled in the art that various modifications and variations can be made in the method for determining the concentration of heparin in a fluid sample and the device for performing this method without departing from the spirit or scope of the invention. Thus, it is intended that the present invention cover the modifications and variations of this invention provided they come within the scope of the appended claims and their equivalents.

What is claimed is:

1. A device for determining the concentration of heparin in a fluid sample, comprising:

a container for holding the fluid sample;

a container for holding the dye solution;

a mixer for mixing the fluid sample and the dye solution;

an illumination source for illuminating a mixture comprising the fluid sample and the dye solution with electromagnetic radiation having a substantially continuous range of wavelengths in the visible range;

a detector for detecting the absorption spectrum of the mixture within the substantially continuous range of wavelengths;

a recorder for recording the absorption spectrum of the mixture within the substantially continuous range of wavelengths; and a calculator for calculating a spectral parameter;

wherein the value of the spectral parameter is indicative of the concentration of heparin present in the fluid sample, and the spectral parameter is representative of both the reduction in the absorption of the free dye in solution and the increase in the absorption of the dye-heparin complex in a method in which the dye solution is added to the fluid sample to form a mixture of sample and dye, and the dye interacts with the heparin in the sample so that the absorption spectrum of the mixture of sample and dye in the visible range varies as a result of the interaction in a manner quantitatively dependent on the heparin concentration.

2. A device according to claim 1, wherein the illumination source for illuminating the composition comprises at least one light-emitting diode having substantially continuous multiple wavelengths in the visible range.

3. A device according to claim 2, wherein the illumination source further comprises at least one diode emitting light in the red region.

4. A device according to claim 1, wherein the container for holding the fluid sample comprises a hollow fiber filter with a porosity to separate the corpuscular portion of blood from the plasma.

5. A device according to claim 4, wherein the device further comprises a holder for holding a detergent solution and a holder for holding a waste solution.

6. A device according to claim 1, wherein the device further comprises a computer.

* * * * *